United States Patent [19]
Williams

[11] Patent Number: 5,824,103
[45] Date of Patent: Oct. 20, 1998

[54] TIBIAL PROSTHESIS

[75] Inventor: Welcome H. Williams, Wayne, N.J.

[73] Assignee: Howmedica Inc.

[21] Appl. No.: 854,827

[22] Filed: May 12, 1997

[51] Int. Cl.⁶ .................................................. A61F 2/38
[52] U.S. Cl. ...................................................... 623/20
[58] Field of Search .............................................. 623/20

[56] References Cited

U.S. PATENT DOCUMENTS

| | | | |
|---|---|---|---|
| 4,257,129 | 3/1981 | Volz | 623/20 |
| 4,550,448 | 11/1985 | Kenna | 623/16 |
| 4,653,488 | 3/1987 | Kenna et al. | 128/92 VW |
| 4,834,756 | 5/1989 | Kenna | 623/16 |
| 4,963,152 | 10/1990 | Hofmann et al. | 623/18 |
| 5,007,933 | 4/1991 | Sidebotham | 623/20 |
| 5,035,700 | 7/1991 | Kenna | 606/88 |
| 5,192,324 | 3/1993 | Kenna | 623/16 |
| 5,194,066 | 3/1993 | Vanzile | 623/20 |
| 5,358,527 | 10/1994 | Forte | 623/20 |
| 5,370,699 | 12/1994 | Hood | 623/20 |
| 5,395,401 | 3/1995 | Bahler | 623/20 |
| 5,405,396 | 4/1995 | Heldreth | 623/20 |
| 5,609,639 | 3/1997 | Walker | 623/20 |
| 5,702,466 | 12/1997 | Pappas | 623/20 |

OTHER PUBLICATIONS

Brochure entitled "Duracon The Tibial System", published by Howmedica, Inc., Rutherford, New Jersey, pp. 1–15, Dec. 1994.

*Primary Examiner*—Michael J. Milano
*Attorney, Agent, or Firm*—Joseph J. Kaliko

[57] ABSTRACT

A tibial prosthesis includes a base support member, a bearing surface member, a stabilizer insert support, and a shoulder screw. The base member has a centrally located proximally flared protrusion or rail which extends substantially from the anterior edge of the base support member to the posterior edge of the base support member and defines a pair of substantially parallel dovetail coupling edges. An upstanding posterior stop is located on the upper surface of the rail adjacent its posterior edge and a posteriorly angled screw hole is provided in an anterior portion of the rail. The bearing member has a lower distally tapered recess or groove, dimensioned to receive the rail on the base member, and a posterior stop receiving recess for permitting the posterior stop on the base member rail to engage the insert support. A hollow upstanding stabilizer is formed on a central portion of the bearing member and a hole is provided anterior of the stabilizer. The stabilizer insert support is generally L-shaped and dimensioned to fit inside the hollow stabilizer portion of the bearing member. The base of the stabilizer insert is provided with a counterbored hole to be engaged by the shoulder screw which is placed through the screw receiving holes of the bearing member and the base member and engaged by threads in the base member.

23 Claims, 7 Drawing Sheets

TIBIAL PROSTHESIS

This application is related to the following U.S. Patents, the complete disclosures of which are hereby incorporated by reference herein: U.S. Pat. Nos. 4,550,448; 4,653,488; 4,834,756; 4,944,756; 5,035,700; and 5,192,324.

BACKGROUND OF THE INVENTION

1. Field of the Invention

The invention relates to prosthetic devices for replacing the proximal tibial surface of a knee joint. More particularly, the invention relates to a tibial baseplate, a tibial insert, an insert support, and a support screw.

2. Description of the Related Art

There are several types of knee prostheses known in the art. One type is sometimes referred to as a "resurfacing type". In these prostheses, the articular surface of the distal femur and proximal tibia are "resurfaced" with respective metal and plastic condylar-type articular bearing components. These knee prostheses provide adequate rotational and translational freedom and require minimal bone resection to accommodate the components within the boundaries of the available joint space. The patella-femoral joint may also be resurfaced by a third prosthetic component as well. The femoral, tibial and patella prosthetic resurfacing components are affixed to respective, surgically prepared adjacent bone structure by a cementing or by a biological bone ingrowth fixation means.

The femoral component is a metallic alloy construction (cobalt-chrome alloy or 6A14V titanium alloy) and provides medial and lateral condylar bearing surfaces of multi-radius design of similar shape and geometry as the natural distal femur or femoral-side of the knee joint. The tibial component usually includes a distal metal base component and a proximal interlocking plastic, e.g. UHMWPE (ultra high molecular weight polyethylene), component or insert. The plastic tibial plateau bearing surfaces are of concave multi-radius geometry to more or less match the articular geometry of the mating femoral condyles. In the resurfacing type of total knee prostheses both the femoral and tibial components are positioned on the respective side of the knee joint and are not mechanically connected or linked together.

The tibial plateau bearing surface geometry can assume a variety of configurations, depending upon the desired extent of articular contact congruency and associated translational (medial-lateral and anterior-posterior) and rotational (axial and varas-valgus) secondary femoro-tibial motions. These various secondary motions allow the resurfaced knee to function in a natural biomechanical manner in conjunction with the surrounding ligamentous and muscle structures about the knee joint. The viable soft tissue structures functionally maintain the femoral and tibial bearing surfaces in contact, provide the necessary levels of constraining force to achieve knee joint stability, and decelerate the principal motion in flexion-extension and secondary motions, such as axial rotation, etc. in a controlled manner. Additionally, this functional interaction between the surrounding tissue structures and the implanted knee prosthesis minimizes abrupt motion stoppage or impact loading of properly designed prosthetic articular surfaces, and thus prevents over stressing at the component fixation interface. Nevertheless, the tibial plateau bearing surface must be sufficiently dimensioned to resist wear and stress. Premature polyethylene wear requires additional surgery and can also result in a fracture of the metallic base plate.

Sometimes the UHMWPE tibial bearing component includes an upwardly extending post-like structure, which is positioned between the plateau bearing surfaces, slightly anterior of the component mid-line. This structure serves as a posterior cruciate ligament substitute to constrain translational movement of the femoral component and is subject to anterior and posterior loading. Usually, the post-like structure is formed as a hollowed extension of the bearing component and a metal insert support is placed in the hollowed extension. These components are sometimes referred to as "stabilizer inserts".

In addition to the material and geometrical requirements of the tibial prostheses, there are significant assembly requirements. That is, the plastic bearing component must be securely attached to the metallic base component and, when used, the metal insert must also be attached to the base component in such a manner to resist shearing stresses. The assembly requirements are of particular concern with "modular tibial prostheses".

Modular prostheses are now widely available for use by orthopedic surgeons. The modular prostheses allow the surgeon to customize the prosthetic device to suit the anatomy of an individual patient. Thus, these modular systems usually provide several different types and sizes of base components and several different types and sizes of plastic bearing components. The prosthesis is assembled by the surgeon just prior to implantation. Therefore, it is important that the prosthesis be easy to assembly without compromising any of the dimensional and mechanical aspects of the prosthesis.

U.S. Pat. No. 5,405,396 to Heldreth et al. discloses a modular tibial prosthesis wherein the plastic bearing member is attached to the metallic base member via a posterior tongue and groove as well as a "dovetail mechanism". A posterior portion of the base member is provided with a groove and a posterior portion of the bearing member is provided with a tongue. The dovetail mechanism consists of a centrally located substantially V-shaped flared projection on the base member and a centrally located substantially V-shaped flared recess on the bottom of the plastic bearing member. The bearing member is thus attached to the base member by placing the bearing member over the base member and slightly anterior relative the midpoint of the base member, then sliding the bearing member posteriorly and downward until the tongue engages the groove and the V-shaped projection engages the V-shaped recess. While this arrangement may provide adequate coupling of the bearing member to the base member in some situations, the engaging surfaces are relatively small. In the case of relatively small prostheses, this configuration will not provide sufficient coupling strength and the bearing member is likely to become detached from the base member. Heldreth et al. also discloses a screw-hole which is centrally located anterior of the V-shaped projection in the base member. The screw-hole is used to receive a screw for fastening a reinforcing component and for attaching a stem extension. However, the location and configuration of the screw and screw-hole subject the screw to shearing strain and posterior loading.

U.S. Pat. No. 4,963,152 to Hofmann et al. discloses an asymmetric prosthetic tibial component wherein the plastic bearing member is coupled to the metallic base member via a pair of posterior tongue and groove couplings and a single central anterior snap lock. This configuration appears to provide even less coupling strength than the configuration disclosed in Heldreth et al.

U.S. Pat. No. 5,358,527 to Forte discloses a total knee prostheses which includes many embodiments. In several embodiments, Forte shows a coupling between a plastic bearing member and a metallic base member which consists of a dovetail type coupling. The base member is provided with a centrally located V-shaped flared projection which widens in the posterior portion and turns outward to form a pair of posterior lips which continue along the medial and lateral edges of the base member. The plastic bearing member is provided with a mating central recess and peripheral flared edges. The flared projection in the base member has an anterior screw hole and the bearing member has a corresponding hole for receiving as screw which further secures the bearing member to the base member. The coupling arrangement shown by Forte would appear to provide a strong coupling between the bearing member and the base member, but it has some disadvantages. The peripheral lip requires that the thickness of the plastic bearing member be reduced at its edges thereby risking premature wear and subsequent fracture of the base member. In addition, the V-shape of the central dovetail will allow for some torsional movement of the bearing member relative to the base member if the screw is not sufficiently tightened or if the screw becomes loose.

SUMMARY OF THE INVENTION

It is therefore an object of the invention to provide a tibial prosthesis having a base member and a bearing member which are coupled to each other such that the bearing member is vertically and torsionally retained by the base member.

It is also an object of the invention to provide a tibial prosthesis having a base member and a bearing member which are securely coupled to each other even when the size of the prosthesis is relatively small.

It is another object of the invention to provide a tibial prosthesis having a base member and a bearing member which are easily coupled to each other.

It is still another object of the invention to provide a tibial prosthesis having a base member and a stabilizing bearing member which includes a reinforcement post.

It is yet another object of the invention to provide a tibial prosthesis having a base member and a stabilizing bearing member which includes a reinforcement post and a securing screw which provides anterior/posterior retention as well as providing increased resistance to posteriorly applied shear loading.

Still another object of the invention is to provide a coupling arrangement for a tibial base plate and insert wherein the thickness of the bearing portions of the insert is not compromised by the coupling arrangement.

In accord with these objects which will be discussed in detail below, the tibial prosthesis of the present invention includes a metallic base support member (base plate), a plastic bearing surface member (insert), a stabilizer insert support, and a shoulder screw. The base plate has a centrally located proximally flared protrusion or rail which extends substantially from the anterior edge of the base plate to the posterior edge of the base plate and defines a pair of substantially parallel dovetail coupling edges. An upstanding posterior stop is positioned in the upper surface of the rail adjacent its posterior edge and a posteriorly angled screw hole is provided in an anterior portion of the rail. The bearing member (insert) has a lower distally tapered recess or groove, dimensioned to receive the rail on the base plate, as well as a posterior stop receiving recess for permitting the posterior stop on the base plate rail to engage the insert support. A hollow upstanding stabilizer is formed on a central portion of the insert and a screw receiving hole is provided in the insert anterior of the stabilizer. The stabilizer insert support is generally L-shaped and dimensioned to fit inside the hollow stabilizer portion of the insert. The base of the support is provided with a counterbored hole to be engaged by the shoulder screw which is placed through the screw receiving holes of the insert and the base plate and engaged by threads in the base plate. The tibial prosthesis is assembled by inserting the stabilizer support into the hollow stabilizer of the insert (typically a preassembled subassembly) so that the hole in the support aligns with the hole in the insert, sliding the insert posteriorly onto the rail of the base plate until the support engages the stop on the rail, inserting the shouldered screw through the holes in the insert and the support, and threading the screw into the threads in the base plate.

The tibial prostheses according to the invention may be made in a variety of sizes and thicknesses and may be as small as 9 mm (the thickness of the bearing surfaces). Additional objects and advantages of the invention will become apparent to those skilled in the art upon reference to the detailed description taken in conjunction with the provided figures.

DETAILED DESCRIPTION OF THE PREFERRED EMBODIMENTS

Referring now to FIGS. 1 through 6, a tibial base plate or support member 10, according to the invention, generally includes a top or proximal symmetrical supporting surface 12 and a lower or distal mounting stem 14. The upper surface 12 is substantially bisected by a proximally flared protrusion or rail 16 which extends substantially the entire anterior-posterior width of the base plate and, as will be described in more detail below, forms the first part of a dovetail coupling. The rail 16 is provided with a posterior upstanding stop 18 and a posteriorly angled (approximately 12½) anterior counterbored screw hole 20. Preferably, the stem 14 is angled posteriorly (approximately 3½) and is buttressed by posteriorly angled (approximately 25½) fins 22, 24. The support member 10 is preferably made of a cobalt chrome (Vitallium) alloy.

Turning now to FIGS. 7 through 12, a stabilizer tibial insert (bearing support member) 30 is a symmetrical plastic (UHMWPE) member having two upper or proximal bearing support surfaces 32, 34 which conform to the distal condyles of a femoral member (not shown), and a centrally located upstanding hollow stabilizer 36 which is dimensioned to serve as a substitute for the posterior cruciate ligament. A screw receiving hole is provided anterior of the stabilizer 36. As seen best in FIGS. 7, 8, and 11, the lower or distal surface 40 of the insert 30 is substantially bisected by a distally tapered groove 42 which is dimensioned to mate with the proximally flared rail 16 of the base plate 10 described above, and which forms the second part of a dovetail coupling. A posterior portion of the groove 42 is provided with a stop receiving slot 44 which allows the insert 30 to pass over the stop 18 on the baseplate 10 ((FIG. 1) as will be described in more detail below. In addition, an insert support receiving well 46 is provided in an area of the groove 42 surrounding the lower hollow access to the stabilizer 36 and the screw hole 38. As will be described in more detail below, this well 46 is dimensioned to receive the base portion of the metallic stabilizer support member.

As mentioned above, the stabilizer insert 30 is intended to be used with a metallic (preferably cobalt chrome alloy) support member. FIGS. 13–16 illustrate a support member 50 according to the invention. The support member 50 is substantially L-shaped having a base portion 52 and a posterior upstanding portion 54. The base portion 52 is provided with a shouldered posteriorly angled (approximately 12½) anterior screw hole 56. The base portion 52 is dimensioned to fit within the well 46 of the insert 30 (FIG. 8) with the upstanding portion 54 extending into the hollow stabilizer 36 and the hole 56 aligned with the hole 38.

From the foregoing, and with reference to FIGS. 17–22, those skilled in the art will appreciate that the aforedescribed components (baseplate 10, insert 30, and support 50) are easily assembled to form a tibial prosthesis 100 which is shown in FIGS. 17–22. As seen best in FIGS. 17 and 22, the first step in the assembly is to place the upstanding portion 54 of the support 50 into the hollow stabilizer 36 of the insert 30 so that the base portion 52 of the support 50 is received in the well 46 of the insert 30 and the hole 56 in the support 50 aligns with the hole 38 in the insert 30. The subassembly resulting from the first step in the assembly process being described is generally made available as a preassembly.

Figure 1:
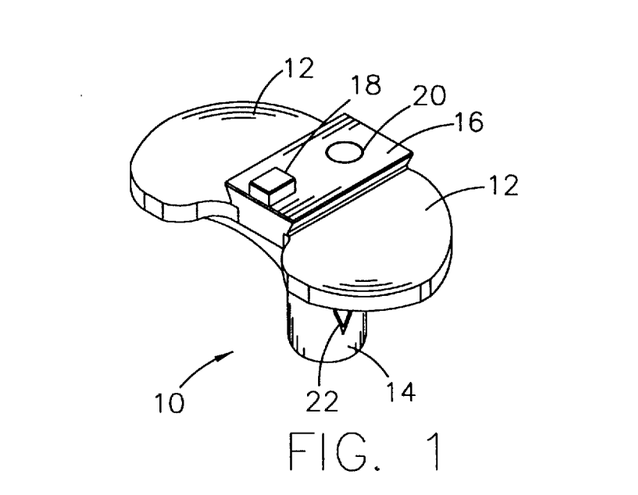
FIG. 1 is a perspective view of the upper or proximal end of a base support member (tibial base plate) according to the invention.
Figure 2:
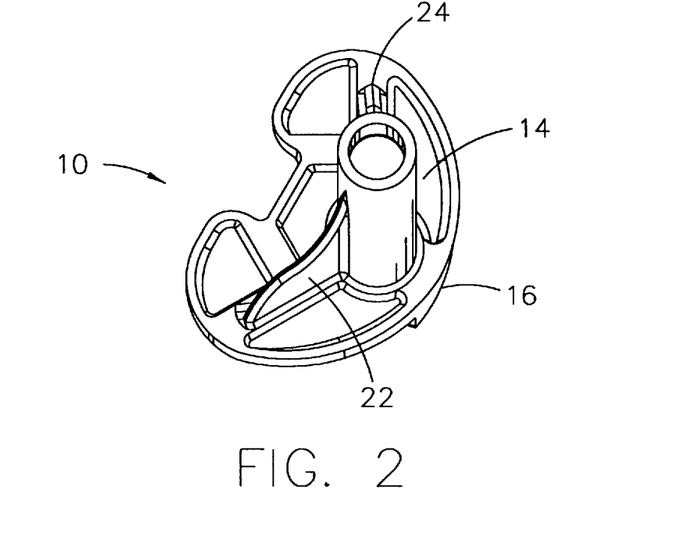
FIG. 2 is a perspective view of the lower or distal end of the base support member of FIG. 1.
Figure 3:
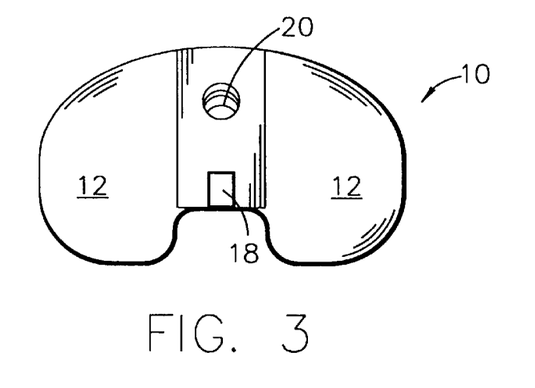
FIG. 3 is a top plan view of the base support member of FIG. 1.
Figure 4:
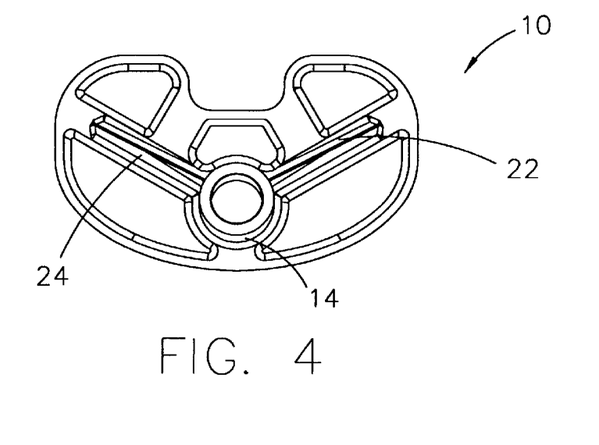
FIG. 4 is a bottom plan view of the base support member of FIG. 1.
Figure 5:
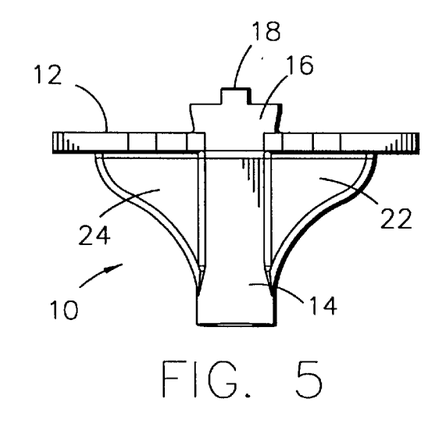
FIG. 5 is a posterior side elevation view of the base support member of FIG. 1.
Figure 6:
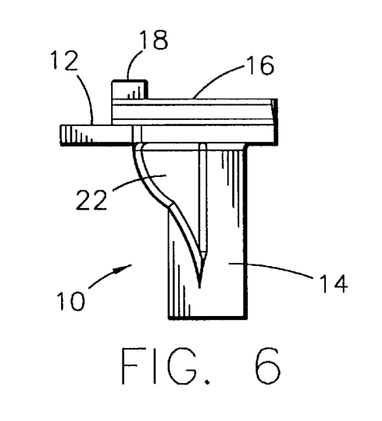
FIG. 6 is medial (or lateral) side elevation view of the base support member of FIG. 1.
Figure 7:
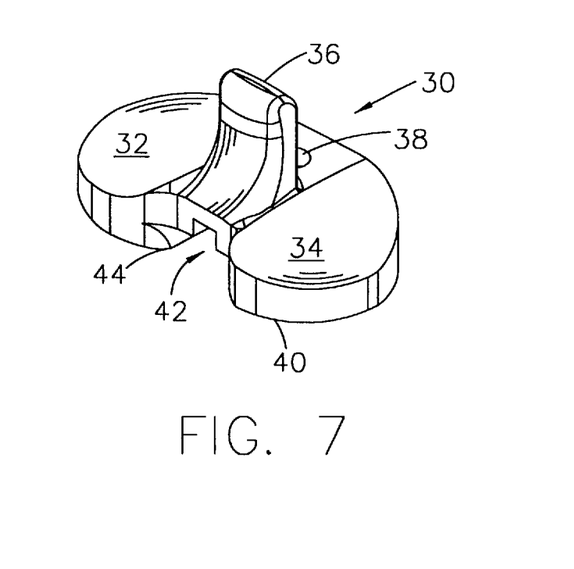
FIG. 7 is a perspective view of the upper or proximal end of a bearing surface member (stabilizer tibial insert) according to the invention.
Figure 8:
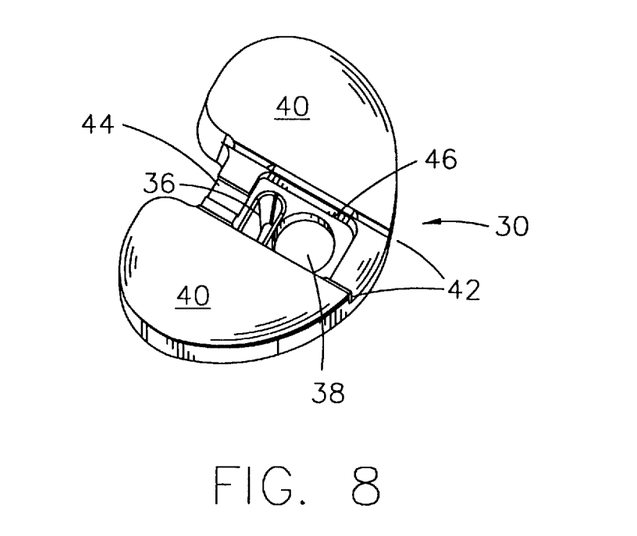
FIG. 8 is a perspective view of the lower or distal end of the bearing surface member of FIG. 7.
Figure 9:
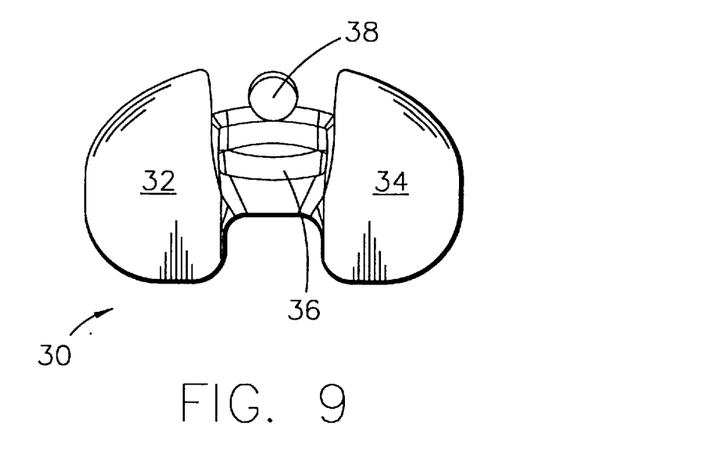
FIG. 9 is a top plan view of the bearing surface member of FIG. 7.
Figure 10:
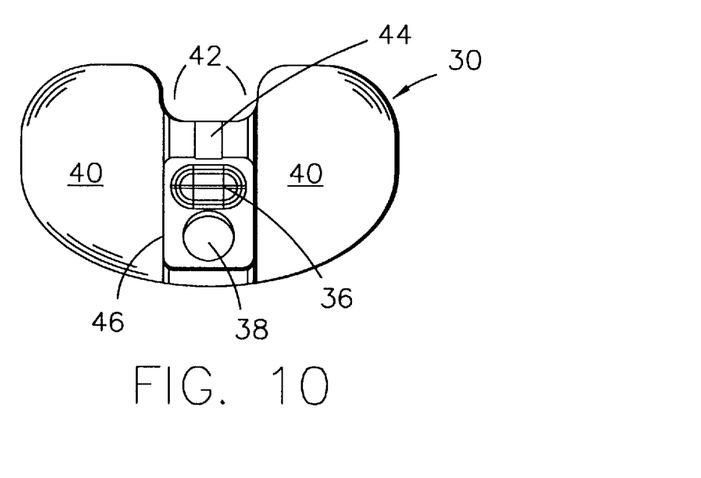
FIG. 10 is a bottom plan view of the bearing surface member of FIG. 7.
Figure 11:
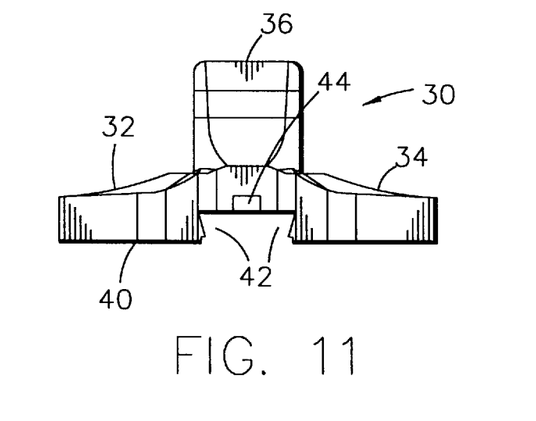
FIG. 11 is a posterior side elevation view of the bearing surface member of FIG. 7.
Figure 12:
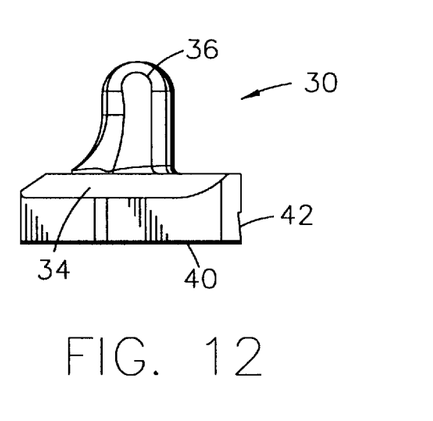
FIG. 12 is medial (or lateral) side elevation view of the bearing surface member of FIG. 7.
Figure 13:
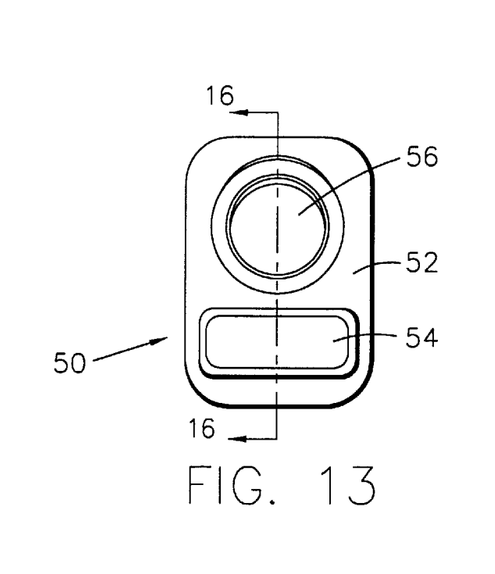
FIG. 13 is a top plan view of a stabilizer insert support according to the invention.
Figure 14:
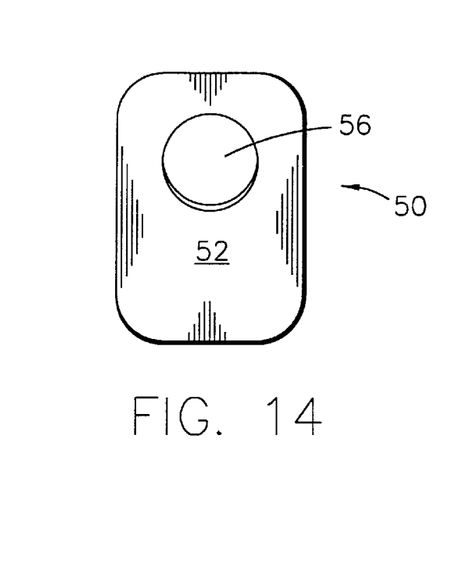
FIG. 14 is a bottom plan view of the support of FIG. 13.
Figure 15:
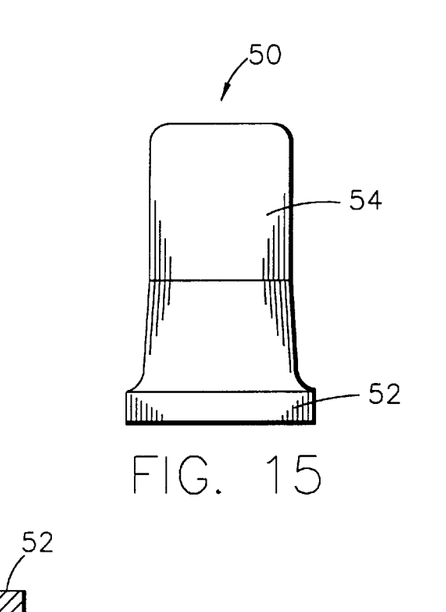
FIG. 15 is a posterior side elevation view of the support of FIG. 13.
Figure 16:
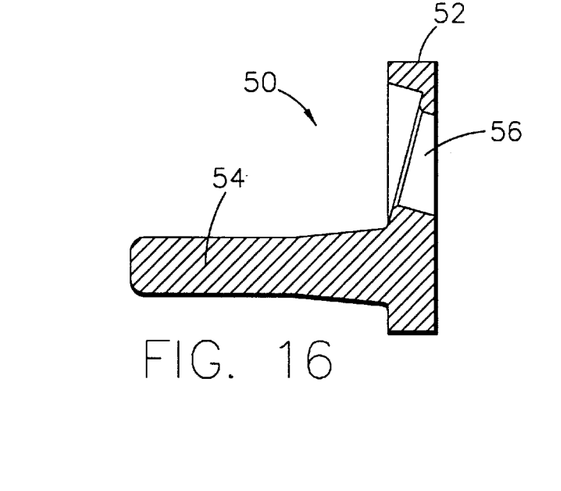
FIG. 16 is a cross sectional view of the support taken along line 16—16 in FIG. 13.
Figure 17:
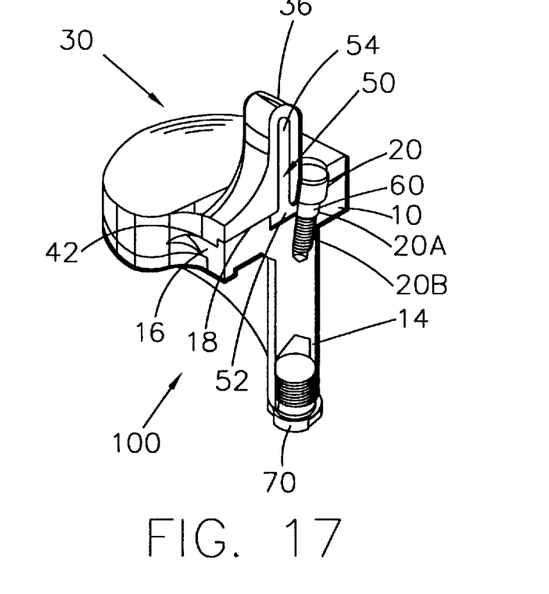
FIG. 17 is a broken perspective view of the upper or proximal end of an assembled tibial prosthesis according to the invention.
Figure 18:
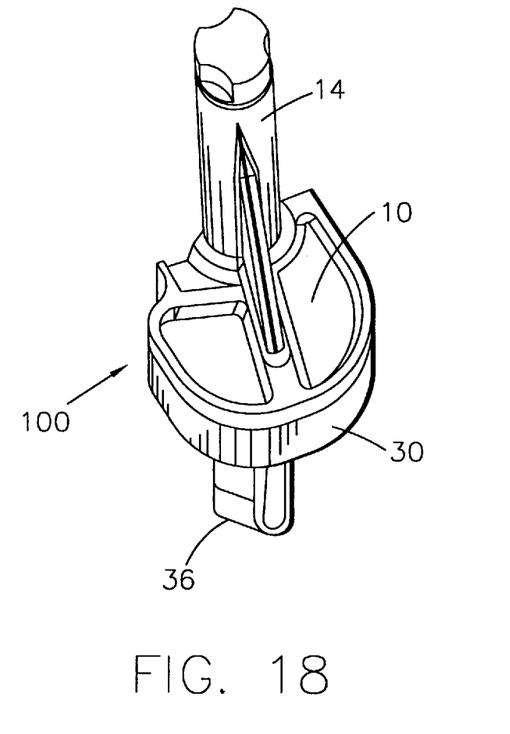
FIG. 18 is a perspective view of the lower or distal end of the tibial prosthesis of FIG. 17.
Figure 19:
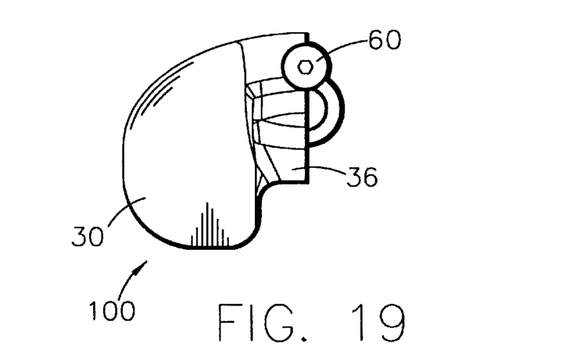
FIG. 19 is a top plan view of the tibial prosthesis of FIG. 17.
Figure 20:
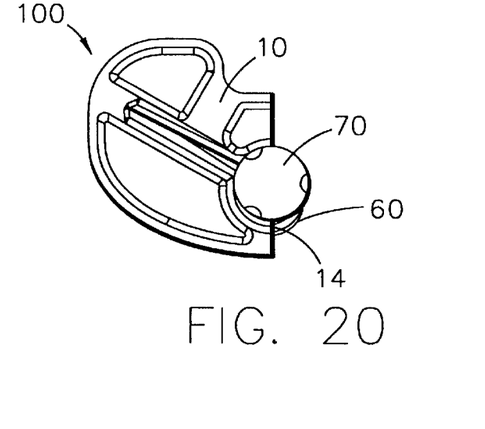
FIG. 20 is a bottom plan view of the tibial prosthesis of FIG. 17.
Figure 21:
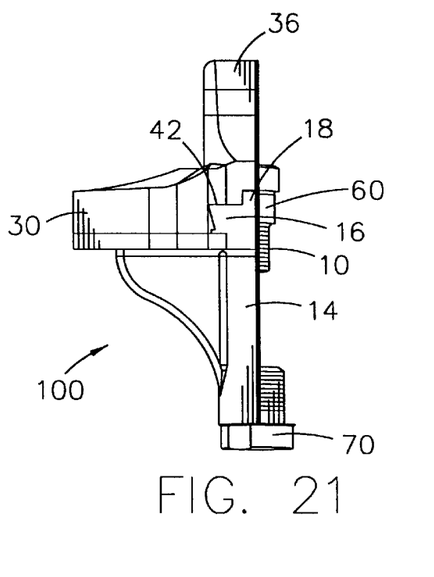
FIG. 21 is a posterior side elevation view of the tibial prosthesis of FIG. 17.
Figure 22:
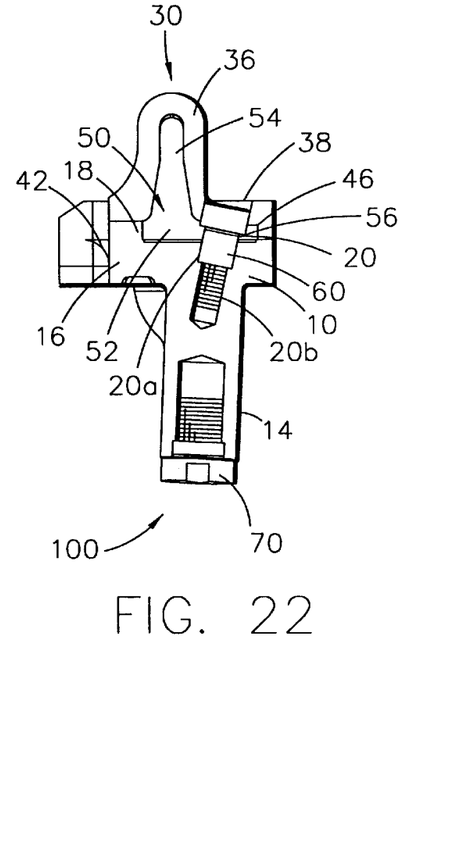
FIG. 22 is medial (or lateral) side elevation view of the tibial prosthesis of FIG. 17.

Next, as seen best in FIGS. 17 and 21, the insert 30, carrying the support 50, is positioned so that its posterior end faces the anterior end of the baseplate 10 and the groove 42 in the insert 30 is aligned with the rail 16 on the baseplate 10. The insert 30 is pushed posteriorly so that the rail 16 is embraced by the groove 42 and the base portion 52 of the support 50 abuts the stop 18 on the baseplate rail 16. The stop 18 prevents further posterior movement of the insert 30 and stops the insert 30 at a location where the hole 38 in the insert and the hole 56 in the support 50 are aligned with the hole 20 in the baseplate 10. With the components 10, 30, and 50 so arranged, a hexagon socket head shoulder screw 60 is inserted into the holes 38, 56, 20 and is screwed into threaded engagement with the baseplate 10. As seen best in FIGS. 17 and 22, the hole 20 in the baseplate 10 has a broad unthreaded upper or proximal portion 20a which receives the shoulder of the screw 60, and a lower or distal narrow threaded portion 20b which receives and engages the threaded portion of the screw 60. As shown in the Figures, the stem 14 of the baseplate 10 is provided with a threaded stem cap 70. This cap may be removed so that a stem extension can be added to stem 14.

From the foregoing, those skilled in the art will appreciate that the central dovetail coupling of the insert 30 to the baseplate 10 will provide excellent torsional as well as vertical retention of the insert. The use of the shoulder screw 60, rather than a conventional socket head screw, provides an added benefit that, in addition to anterior-posterior retention of the insert, the screw is highly resistant to posteriorly applied shear loading. The increased resistance to shear loading is achieved by the larger diameter shoulder portion of the screw 60 and the lack of stress risers which are found in conventional screws due to their thread configuration. Furthermore, the prosthesis 100 is very easy to assemble and does not require very careful positioning of the components at the time of the assembly. Assembly does not require deformation of the insert as is required in many of the prior art devices. The coupling of the insert to the base plate also does not interfere with the thickness of the bearing portions of the insert.

As mentioned above, the tibial prosthesis of the invention may be made in several different sizes. According to one exemplary embodiment, the baseplate 10 has a medial-lateral width of approximately 2.44 inches and an anterior-posterior width of approximately 1.44 inches. In this embodiment, the thickness of the base plate at the supporting surface 12 is approximately 0.117 inches, the height of the rail 16 is approximately 0.173 inches, and the height of the stop 18 is approximately 0.286 inches relative to the supporting surface 12. The angle of the flare in the rail 16 is preferably approximately 60½. The stem 14 is approximately 1.18 inches long and has an outer diameter of approximately 0.525 inches. The insert 30 will have corresponding dimensions to fit on the baseplate 10. According to the exemplary embodiment, the thickness of the bearing portions 32, 34 of the insert 30 (at pre-established gauge points) will range from approximately 0.430 inches to approximately 0.247 inches. In this embodiment, the overall height of the insert (including the stabilizer 36) is approximately 1.174 inches. The support 50 used in the exemplary embodiment has an overall height of approximately 0.748 inches. The base portion of the support is approximately 0.505 inches by 0.729 inches and the diameter of the hole in the base portion is stepped from approximately 0.356 inches to approximately 0.258 inches. The shoulder screw 60 in this embodiment is approximately 0.635 inches long with a threaded length of approximately 0.220 inches and a shoulder diameter of approximately 0.239 inches.

There have been described and illustrated herein components of a tibial prosthesis and an assembled tibial prosthesis. While particular embodiments of the invention have been described, it is not intended that the invention be limited thereto, as it is intended that the invention be as broad in scope as the art will allow and that the specification be read likewise. Thus, while particular dimensions have been disclosed, it will be appreciated that other dimensions could be utilized. Also, while particular angles have been shown, it will be recognized that other angles could be used with similar results obtained. Moreover, while particular configurations have been disclosed in reference to the stop, it will be appreciated that other configurations could be used as well. Furthermore, while the prosthesis has been disclosed as being made from particular materials, it will be understood that different materials can achieve the same or similar function as disclosed herein. It will therefore be appreciated by those skilled in the art that yet other modifications could be made to the provided invention without deviating from its spirit and scope as so claimed.

What is claimed is:

1. A tibial prosthesis comprising:
   a) a base support member having a proximal supporting surface and a single integrally formed centrally located proximally flared protrusion which substantially bisects said supporting surface; and
   b) a bearing surface member having a pair of proximal bearing surfaces and a single distal distally tapered groove, said distally tapered groove dimensioned to slideably embrace said single integrally formed centrally located proximally flared protrusion.

2. A tibial prosthesis according to claim 1 wherein said single integrally formed centrally located proximally flared protrusion defines a pair of substantially parallel dovetail coupling edges.

3. A tibial prosthesis according to claim 1 wherein said base support member has a first screw receiving hole located in an anterior portion of said single integrally formed centrally located proximally flared protrusion, and said bearing surface member has an anterior second screw receiving hole which is aligned with said first screw receiving hole when said single distal distally tapered groove embraces said single integrally formed centrally located proximally flared protrusion.

4. A tibial prosthesis according to claim 3 further comprising:
   c) a shoulder screw dimensioned to pass through said second screw receiving hole and to engage threads in said first screw receiving hole.

5. A tibial prosthesis according to claim 4 wherein said bearing surface member has a centrally located upstanding hollow stabilizer.

6. A tibial prosthesis according to claim 5 further comprising:
   d) a substantially L-shaped support member having a base portion and an upstanding portion, said base portion including a counterbored third screw receiving hole and said upstanding portion dimensioned to fit inside said hollow stabilizer, wherein said shoulder screw is dimensioned to engage said base portion via said third screw receiving hole.

7. A tibial prosthesis according to claim 6 wherein said single integrally formed centrally located proximally flared protrusion has an upstanding posterior stop which abuts said support member when said first, second and third screw receiving holes are aligned.

8. A tibial prosthesis comprising:
   a) a base support member having a proximal supporting surface, a single integrally formed centrally located first dovetail coupling which substantially bisects said supporting surface, and an anterior first screw receiving hole having a distal threaded portion and a proximal unthreaded portion;
   b) a bearing surface member having a pair of proximal bearing surfaces, a single distal second dovetail coupling, and an anterior second screw receiving hole, said single distal second dovetail coupling being dimensioned to mate with said single integrally formed centrally located first dovetail coupling with said first and second screw receiving holes being aligned with each other; and
   c) a shoulder screw dimensioned to pass through said second screw receiving hole and engage said distal threaded portion of said first screw receiving hole.

9. A tibial prosthesis according to claim 8 wherein said bearing surface member has a centrally located upstanding hollow stabilizer.

10. A tibial prosthesis according to claim 9 further comprising:
    d) a substantially L-shaped support member having a base portion and an upstanding portion, said base portion including a counterbored third screw receiving hole and said upstanding portion dimensioned to fit inside said hollow stabilizer, wherein said shoulder screw is dimensioned to engage said base portion via said third screw receiving hole.

11. A tibial prosthesis according to claim 10 wherein said single integrally formed centrally located first dovetail coupling has an upstanding posterior stop which abuts said support member when said first, second and third screw receiving holes are aligned.

12. A tibial prosthesis comprising:
    a) a base support member having a proximal supporting surface and a centrally located first dovetail coupling with an upstanding posterior stop;
    b) a bearing surface member having a pair of proximal bearing surfaces, an upstanding hollow stabilizer, and a centrally located distal second dovetail coupling, said second dovetail coupling dimensioned to slideably embrace said first dovetail coupling; and
    c) a stabilizer support member dimensioned to fit inside said upstanding hollow stabilizer and abut said posterior stop when said second dovetail coupling slideably embraces said first dovetail coupling.

13. A tibial insert for use with a tibial baseplate having a proximal supporting surface and a single integrally formed centrally located proximally flared protrusion which substantially bisects said supporting surface, said insert comprising a bearing surface member having a pair of proximal bearing surfaces and a single distal distally tapered groove, said single distally tapered groove dimensioned to slideably embrace said single integrally formed centrally located proximally flared protrusion.

14. A tibial insert according to claim 13 wherein said bearing surface member has a centrally located upstanding hollow stabilizer and an anterior screw receiving hole.

15. A tibial base plate for use with a tibial insert having a pair of proximal bearing surfaces and a single distal distally tapered groove, said base plate comprising a base support member having a proximal supporting surface and a single integrally formed centrally located proximally flared protrusion which substantially bisects said supporting surface and which is dimensioned to slideably embrace said distally tapered groove.

16. A tibial base plate according to claim 15 further comprising an upstanding stop located on a posterior portion of said single integrally formed centrally located proximally flared protrusion.

17. A tibial base plate according to claim 15 wherein said single integrally formed centrally located proximally flared protrusion has an anterior screw receiving hole, said hole having a distal threaded portion and a proximal unthreaded portion.

18. A tibial base plate according to claim 17 wherein said screw receiving hole is dimensioned to receive a shoulder screw.

19. A method for assembling a tibial prosthesis comprising the steps of:
  a) obtaining a base support member having a proximal supporting surface and a single integrally formed centrally located proximally flared protrusion which substantially bisects said supporting surface;
  b) obtaining a bearing surface member having a pair of proximal bearing surfaces and a single distally tapered groove; and
  c) sliding the bearing surface onto the base support member so that the single distally tapered groove embraces said single integrally formed centrally located proximally flared protrusion.

20. A method for assembling a tibial prosthesis comprising the steps of:
  a) obtaining a base support member having a proximal supporting surface, a single integrally formed centrally located first dovetail coupling which substantially bisects said supporting surface, and an anterior first screw receiving hole having a distal threaded portion and a proximal unthreaded portion;
  b) obtaining a bearing surface member having a pair of proximal bearing surfaces, a single distal second dovetail coupling, and an anterior second screw receiving hole;
  c) obtaining a shoulder screw dimensioned to pass through the second screw receiving hole and engage the distal threaded portion at the first screw receiving hole;
  d) sliding the bearing surface member onto the base support member such that said second dovetail coupling mates with said single integrally formed centrally located first dovetail coupling and the first and second screw receiving holes are aligned with each other;
  e) inserting the shoulder screw through the first and second screw receiving holes; and
  f) threading the screw into the threaded portion of the first screw receiving hole.

21. A method according to claim 20 further comprising the steps of:
  g) obtaining a substantially L-shaped support member having a base portion and an upstanding portion, the base portion including a counterbored third screw receiving hole, the bearing surface member having a hollow stabilizer portion dimensioned to receive the upstanding portion; and
  h) prior to said step of sliding, inserting the upstanding portion of the support member into the stabilizer portion so that the third screw receiving hole is aligned with the second screw receiving hole.

22. A method for assembling a tibial prosthesis comprising the steps of:
  a) obtaining a base support member having a proximal supporting surface, a single integrally formed centrally located first dovetail coupling which substantially bisects said supporting surface and an upstanding posterior stop;
  b) obtaining a bearing surface member having a pair of proximal bearing surfaces, an upstanding hollow stabilizer, and a single centrally located distal second dovetail coupling;
  c) obtaining a stabilizer support member dimensioned to fit inside said upstanding hollow stabilizer;
  d) inserting said stabilizer support member into said hollow stabilizer; and
  e) sliding the bearing surface member onto said base support member so that said single centrally located second dovetail coupling embraces said single integrally formed centrally located first dovetail coupling and said stabilizer support abuts said posterior stop.

23. A method for assembling a tibial prosthesis, comprising the steps of:
  a) obtaining a base support member having a proximal supporting surface and a centrally located first dovetail coupling with an upstanding posterior stop;
  b) obtaining a bearing surface member having a pair of proximal bearing surfaces, an upstanding hollow stabilizer having a stabilizer support member inserted therein, and a centrally located distal second dovetail coupling; and
  c) sliding the bearing surface member onto the base support member so that second dovetail coupling embraces the first dovetail coupling and the stabilizer support abuts the posterior stop.

* * * * *